US008834794B2

(12) United States Patent
Yazdanpanah et al.

(10) Patent No.: US 8,834,794 B2
(45) Date of Patent: Sep. 16, 2014

(54) APPARATUS AND METHODS FOR DETECTION OF TUMOR CELLS IN BLOOD

(76) Inventors: Mehdi M Yazdanpanah, Louisville, KY (US); Romaneh Jalilian, Lousiville, KY (US)

(*) Notice: Subject to any disclaimer, the term of this patent is extended or adjusted under 35 U.S.C. 154(b) by 385 days.

(21) Appl. No.: 13/302,650

(22) Filed: Nov. 22, 2011

(65) Prior Publication Data

US 2012/0129192 A1 May 24, 2012

Related U.S. Application Data

(60) Provisional application No. 61/416,216, filed on Nov. 22, 2010.

(51) Int. Cl.
*G01N 27/00* (2006.01)
*C12M 3/06* (2006.01)
*G01N 33/50* (2006.01)
*B01L 3/00* (2006.01)
*C12M 1/34* (2006.01)

(52) U.S. Cl.
CPC .......... *C12M 23/16* (2013.01); *B01L 2400/086* (2013.01); *B01L 2300/0816* (2013.01); *G01N 33/5094* (2013.01); *B01L 2300/0645* (2013.01); *B01L 2200/0668* (2013.01); *B01L 3/502761* (2013.01); *C12M 41/36* (2013.01); *B01L 2300/0883* (2013.01)
USPC ... 422/82.02; 435/7.1; 435/283.1; 435/287.1; 435/287.9; 436/518; 436/525; 436/149; 422/50; 422/82.01; 422/68.1

(58) Field of Classification Search
CPC .......... B01L 3/5027; B01L 3/502761; B01L 2300/0645; G01N 33/48; G01N 33/5438; G01N 33/5044; G01N 33/483; G01N 33/4836; G01N 33/5094

USPC .......... 435/7.1, 283.1, 287.1, 287.9; 436/518, 436/525, 149; 422/50, 82.01, 68.1, 82.02
See application file for complete search history.

(56) References Cited

U.S. PATENT DOCUMENTS

| | | | | |
|---|---|---|---|---|
| 6,387,707 B1 * | 5/2002 | Seul et al. | ..................... | 436/164 |
| 6,440,662 B1 * | 8/2002 | Gerwen et al. | ............... | 435/6.11 |
| 7,225,780 B2 * | 6/2007 | Khami et al. | ............ | 123/184.57 |
| 8,241,892 B2 * | 8/2012 | Greenberger et al. | ...... | 435/286.1 |
| 8,243,270 B2 * | 8/2012 | Kuo et al. | ..................... | 356/301 |
| 2003/0226768 A1 * | 12/2003 | Hoffman et al. | ........... | 205/777.5 |
| 2004/0011651 A1 * | 1/2004 | Becker et al. | ................. | 204/547 |
| 2007/0187248 A1 * | 8/2007 | Hodko et al. | ................. | 204/547 |
| 2009/0061451 A1 * | 3/2009 | Achim et al. | ..................... | 435/6 |
| 2009/0191616 A1 * | 7/2009 | Lu et al. | ..................... | 435/287.2 |
| 2009/0229980 A1 * | 9/2009 | Hughes et al. | ................ | 204/547 |
| 2009/0243584 A1 * | 10/2009 | Zhang et al. | ................. | 324/71.1 |
| 2010/0140111 A1 * | 6/2010 | Gimsa et al. | ............... | 205/777.5 |
| 2014/0061049 A1 * | 3/2014 | Lo et al. | ..................... | 204/547 |

* cited by examiner

Primary Examiner — Melanie Y Brown

(57) ABSTRACT

In one embodiment, the present invention provides the description of an inexpensive and disposable handheld device for detecting Circulating tumor cells (CTC) in blood called a handheld CTC detector (HCTCD). The HCTCD is capable of detecting less than 1 CTC per milliliter. The HCTCD consists of a dense array of high aspect ratio freestanding metallic nanoneedles, functionalized with antibodies that integrated within a microfluidic device and selectively capture and count (using electrical signal detection) the CTCs. By selecting a right functionalization protocol for the nanoneedles array, the HCTCD can be used for selective capturing a variety of rare cells that are mixed in human fluids.

11 Claims, 13 Drawing Sheets

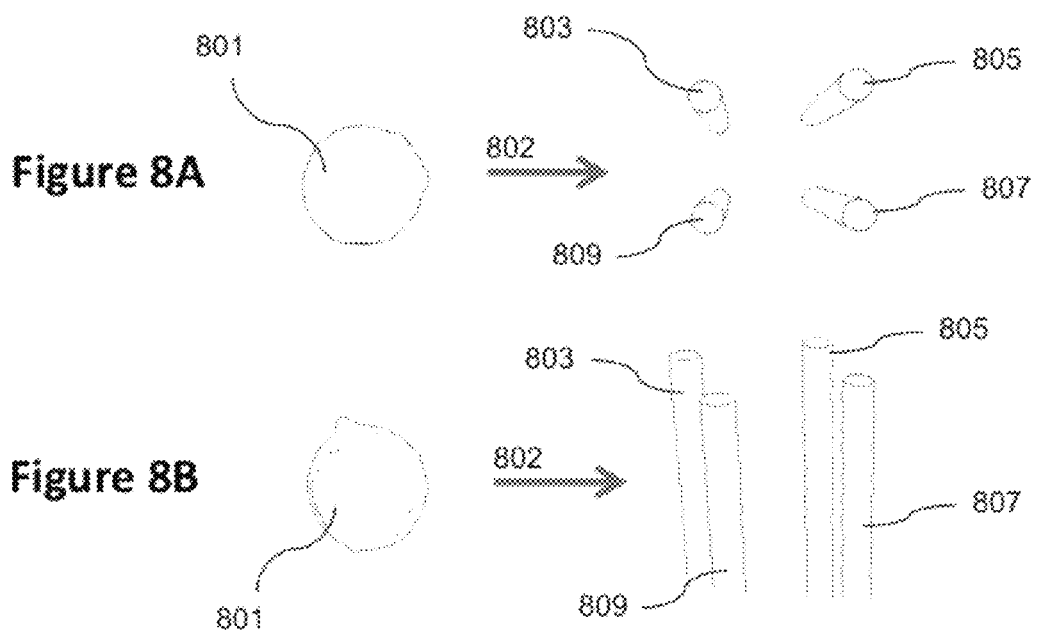

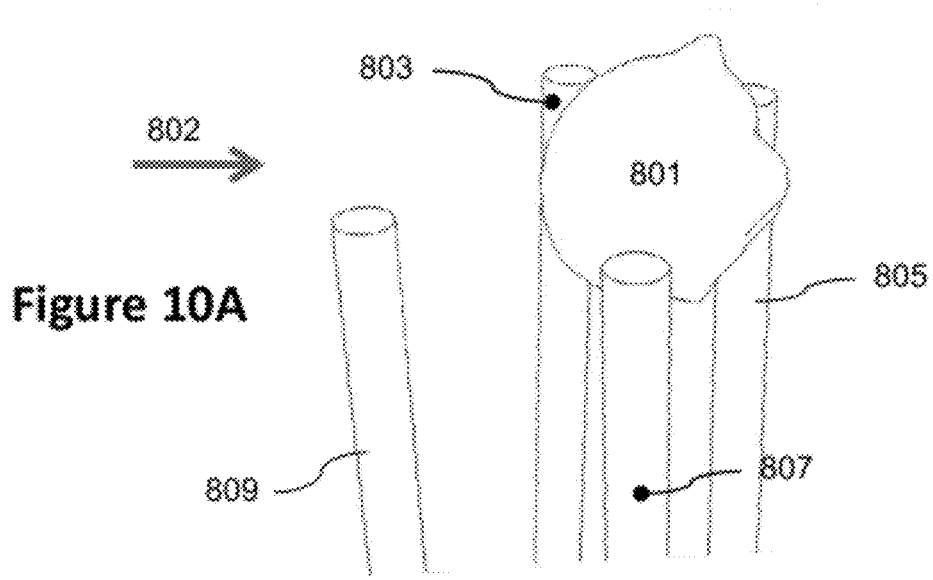
Figure 10A
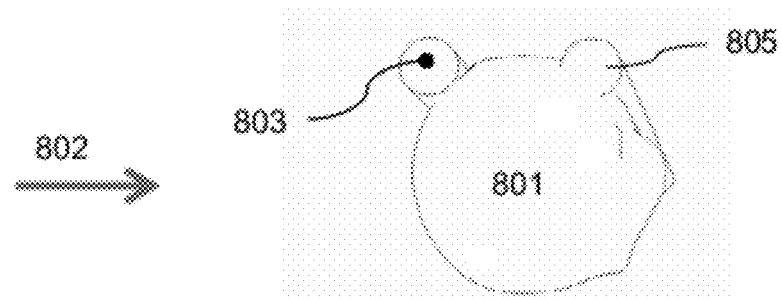
Figure 10B
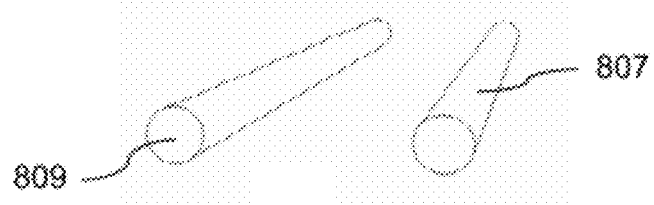

APPARATUS AND METHODS FOR DETECTION OF TUMOR CELLS IN BLOOD

This application claims the benefits of the provisional patent application No. 61/416,216 filed on Nov. 22, 2010.

STATEMENT OF GOVERNMENT INTEREST

This invention was made with Government support under Grant # IIP-1059286 from National Science Foundation, Grant #KSTC184-512-10-082 awarded by Kentucky Science Technology Corporation, and Grant #KSTC184-512-10-107 awarded by Kentucky Science Technology Corporation, and the National Science Foundation under Grant # IIP-1059286 to the American Society for Engineering Education. The government has certain rights in the invention.

BACKGROUND OF THE INVENTION

Circulating tumor cells (CTC) are cells that have detached from primary tumors, and entered the blood stream. They have the potential to seed new tumors at distant sites causing propagation and metastases. It is estimated that in a cancer patient, more than 1 million tumor cells per gram of tumor tissue enter the bloodstream every day. This shedding process is discontinuous, and detected CTC are heterogeneous, some destined to never succeed at implantation. Indeed, colonization of distant organs by CTC is an extremely inefficient process, and the vast majority of these cells may either be destroyed in the circulation, or become dormant at distant sites due to the absence of proper growth regulatory niches. However, once metastasis is established, the subsequent seeding of cancer cells may become much more efficient and deadly. Inherent to this is the amplification and change of the CTC pool during the sequential cycles of cancer cell dissemination. While many questions surrounding these events remain unanswered, the accurate detection and characterization of CTC may shed new light on the aggressiveness and metastases potential of the underlying disease. Thus early detection of low counts of CTCs per blood sample is extremely important as it can be used as a valuable indicator for patients and doctors for diagnosis and to block metastases.

CTCs dimensions may range between ~5-15 µm in diameter and are slightly larger than red blood cells (erythrocytes or RBCs) that are biconcave in shape and ~8 µm in diameter and 2 µm in height, but no larger than the white blood cells (WBCs or leukocytes) that are spherical in shape and 8-15 µm in diameter. Therefore, the detection and separation of the CTCs is extremely difficult using standard cell separation technologies. The outstanding question is, "How can we detect 1 to 10 CTCs mixed with 5 billion red and white blood cells!?"

There have been several efforts by other researchers to capture and quantify low doses of CTCs in patients' blood but due to technological hurdles it has been very difficult to accurately count and detect CTCs at early stages of cancer development since these cells are rare. The ideal CTC detector system should have the following characteristics: (1) accurately detect and count CTC cells, (2) count the number of CTCs in short period of time (within a few minutes), (3) use peripheral blood sample without requiring any purification or enrichment methods, (4) inexpensive so it can be acquired by several clinical setting, (5) simple enough to be used by primary physician, nurse practitioners and technicians, and (6) portable enough to administer such testing at distant sites similar to point of care testing.

Current Methods for CTC Detection

CTC detection methods can be classified into two types: (1) immunological assays that use monoclonal antibodies, and (2) Polymerase Chain Reaction (PCR) based methods that detect tumor specific antigens. Immunological methods have been widely used for CTC detection. The choice of appropriate markers is a challenge as antigens exclusively expressed by CTC and not shared by other circulating non-tumor or blood cells are scarce. Antibodies specific to epithelial antigens such as cytokeratin, and epithelial cell adhesion molecule (EpCAM) are the most widely used markers for epithelial tumor cell detection. Organ-specific markers, including prostate specific antigen (PSA), carcinoembryogenic antigen (CEA) or HER-2 have also been used. However, they are prone to false-negative/positive results as these markers are not necessarily present in all tumor cells (only up to 30% of cancer cells carry HER-2 in HER-2-positive breast cancer) or are not entirely organ specific. More recently prostate specific membrane antigen (PSMA) based CTC detectors have been created that can detect prostate cancer cells with high efficiency. Several immunofluorescence-based technologies are being used and aim to improve the threshold of detection. Enrichment methods with anti-cytokeratin or combination of anti-cytokeratin and anti-EpCAM antibodies have shown to improve the enrichment process for CTCs that has low EpCAM expression.

Several technologies are available for detection of CTCs in blood. Traditionally, density gradient centrifugation is the method that has been used for isolation of CTCs for microscopy. Heavier components in the blood with higher sedimentation rates are separated from the lighter mononuclear components including tumor cells. These are then transferred to slides and stained for epithelial markers such as EpCAM to detect CTC. A trained pathologist should examine the slides for CTC in a time consuming process (one to several days for each sample), subject to false positives and/or false negatives depending on the skill of the operator. Moreover density gradient centrifugation has only a recovery rate of 70%. The downfall of using many of these gradient liquids is that whole blood tends to mix with the gradient if not centrifuged immediately; therefore, interrupting total separation.

Isolation of CTCs using polycarbonate filters have been demonstrated in the past. It is inexpensive and a simpler form of enrichment and capture of CTC. The polycarbonate filters have track etching that results in random placement of pores. This results in low density, and often results in fusion of two or more pores together. They have claimed efficiency of capture is 50-60%. In one of the new devices, paralyne C microfilter assembly is used as a modified form of polycarbonate filters for the capture of CTCs with a yield of 90%. In general most polycarbonate filters suffer from the some drawbacks as mentioned above making it prone to produce false positive or negative results.

CellSearch (Veridex) is the first wide spread CTC detector that has been approved by the Food and Drug Administration (FDA). It works for epithelial cancers namely breast, colon and prostate cancers. The system is based on the enumeration of epithelial cells, which are separated from the blood by antibody coated magnetic beads and identified using fluorescently labeled antibodies against cytokeratin and with a fluorescent nuclear stain and fluorescent cytokeratin antibodies. In their original study using the Veridex system, a total of 177 breast cancer patients were enrolled and tested for their CTC counts over a period of two years. Outcomes were assessed according to levels of CTCs at the baseline, before patients started a new treatment for metastatic disease. It was found that patients in a training set with levels of CTC cells equal to or higher than 5 CTCs per 7.5 ml of whole blood, as compared to with fewer than 5 CTC per 7.5 ml, had a shorter median free progression survival and a shorter overall survival. Systems such as CellSearch, however, suffer from several drawbacks. Multiple steps of batch purification and enrichment result in CTC loss. The actual number of CTCs might be much higher to start within each patient group. Secondly, it might be difficult to fish out cells that do not express EpCAM, possibly because the cells have undergone epithelial mesenchymal transformation (EMT), which makes the cells less susceptible to stick to the antibodies as they break free into the blood circulation. EpCAM methods are also not useful for non-epithelial cancers such as sarcomas. Nevertheless, this is the only FDA approved CTC detector currently in the market.

Another technology that uses passive microfluidic sorting of cells in blood is the CTC chip. The CTC chip has 78,000 micro-posts that is etched in silicon. Antibodies such as EpCAM are functionalized on the surface of the micro-posts. Anti-EpCAM provides the specificity for CTC capture from unfractionated blood as it is overexpressed in epithelial cells and is absent in hematologic cells. The CTC chip measured the number of CTCs in peripheral blood of patients with metastatic lung, prostate, pancreatic, breast and colon cancer in 115 of 116 samples with a range of 5-1,281 CTCs per ml and approximately 50% purity. The CTC chip efficiency depends on the velocity of the blood flow and the resulting drag force on the cells, because it influences the duration of the cell-micropost contact and the chance of subsequent attachment. Therefore, the flow rates are kept extremely low in the order of 1.0 ml/hr. With such a small flow rate, the CTC chip essentially takes 6-8 hours of sorting time for one sample of 7.5 ml of patient blood, followed by confocal microscopy. The yield of this CTC capture is less than 20% at 3.0 ml/hr flow rates. The shear forces around micro-post also make the cell circumvent around the posts thereby making this device prone to false negative results.

Therefore there is need for a portable Circulating Tumor Cell (CTC) detector, such as one example of the present invention that can detect less than 10 CTCs per milliliter in a patient's blood. The ideal CTC detector should utilize pure blood as extracted from the patient blood before any purification or additional enrichment steps, which may increase the probability of losing CTCs. Also the ideal CTC detector must be inexpensive, disposable and fast so it can be used in a physician's office and reveal the results in a few minutes. With recent progress in micro and nano fabrication technology, it is now possible to adopt new approaches to capture and count CTCs. Some of these methods are; isolation of CTCs using polycarbonate filters, Parylene micro-filters nanotube biosensor, Ferro Fluid/Magnetic nanoparticles and three dimensional nanostructured array to capture and count CTCs. However, due to challenges associated with each of these methods, the fabrication of a handheld CTC detector with sub 10 CTCs per ml is still not a reality.

SUMMARY OF THE INVENTION

In one embodiment of the present invention, a nanostructure-based sensing platforms, a handheld CTC detector (HCTCD) with sensitivity of less than 10 CTCs per milliliter HCTCD can:

(a) Capture CTCs (as determined by antibody based binding using CTC specific antibodies such as EpCAM, and Her2 for CTCs in breast cancer) without capturing the remaining ($\sim 5\times 10^9$) RBCs and WBCs, (b) Interrogate all cells in the blood sample including CTCs, RBCs and WBCs to guarantee that all the CTCs are captured without bypassing the capturing sites, (c) Have a very large quantity of capturing sites in order to have a fast capturing rate, (d) Integrate within a microfluidic channel to provide appropriate flow rates to allow target cell binding while at the same time ensuring sufficient sample processing to attain a quantifiable number of CTCs, and (e) Work based on electronic signal detection methods in order to become a handheld and inexpensive device. Electronic signals are much faster than mechanical flow based CTC detection systems. The signal is OFF when no CTC is captured and ON when one or more CTC are trapped by the capturing sites. Based on the number of CTCs that are captured, the electronic signal (e.g. electrical conductance) is stronger.

BRIEF DESCRIPTION OF THE DRAWINGS

FIG. 3a shows an array of Ag2Ga nanoneedles grown on an interdigitated micro electrode.

FIG. 3b shows coated nanoneedles exposed by selectively dipping into $K_2PtCl_4$.

FIG. 3c shows nanoneedles before coating. FIG. 3d shows nanoneedles after coating and functionalization by anti-EpCAM.

FIG. 3e shows the nanoneedle array is integrated into a micro-fluidic device. It shows the step by step fabrication of the proposed HCTCD (100, 700) in one embodiment of the present invention.

FIGS. 8 through 12 show the process by which a CTC is captured (trapped) by four nanoneedles as one embodiment of the present invention.

FIGS. 8A and 8B illustrates the manner CTCs approach four nanoneedles that each are connected to the interdigitated electrodes (not shown in the figure) in one embodiment of the present invention.

FIGS. 10A and 10B illustrates the contact of the CTC with two nanoneedles as viewed from top and side, respectively.

DETAILED DESCRIPTION OF THE PREFERRED EMBODIMENTS

One embodiment of the present invention, HCTCD, can reliably, and reproducibly capture and count (using electrical signal detection) the number of CTCs as low as 1 to 10 cells in 1 ml of pure blood cells. In one embodiment, HCTCD consists of dense array of high aspect ratio freestanding metallic nanoneedles functionalized with antibodies (e.g. anti-EpCAM).

Figure 1:
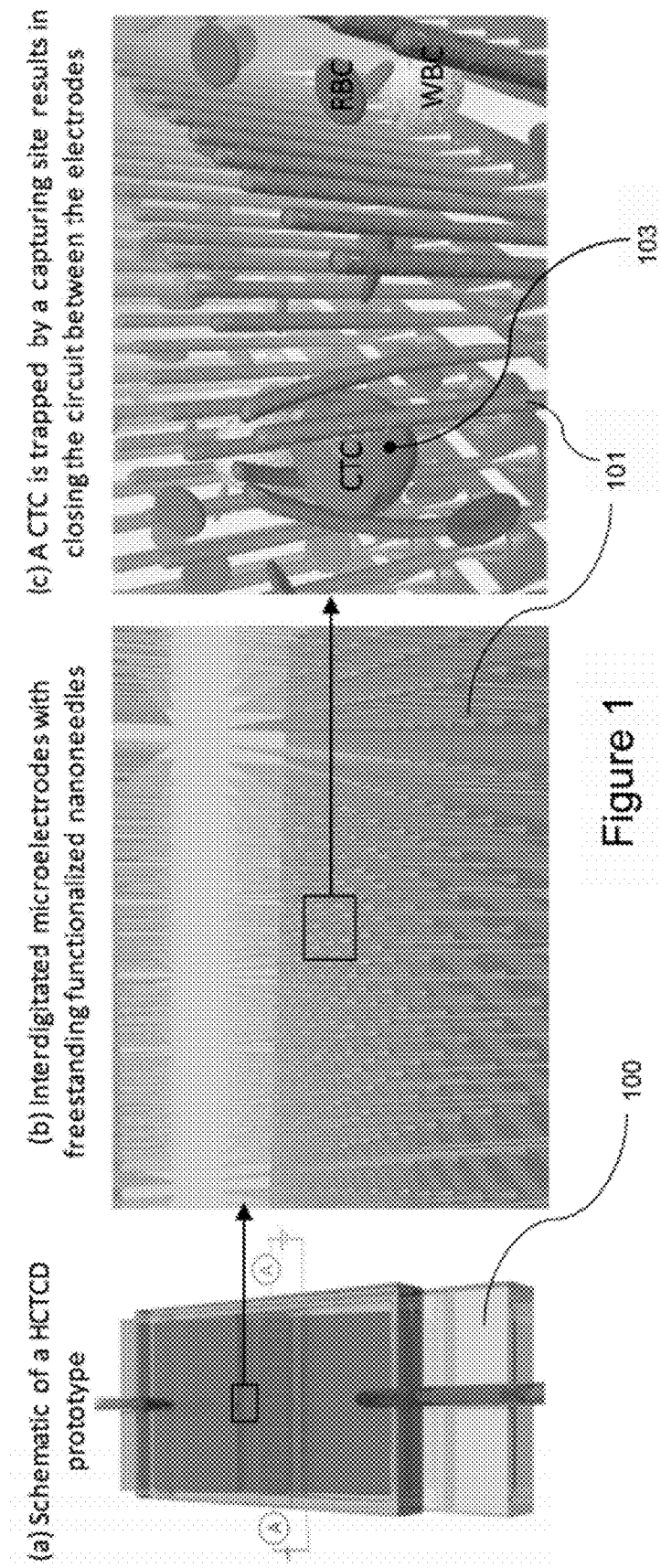
FIG. 1a shows a schematic of the HCTCD prototype that is packaged in a micro-fluidic channel
FIG. 1b shows a close up view of the nanoneedles array with interdigitated microelectrodes
FIG. 1c shows a close up view of HCTCD capturing sites as a CTC has been captured by a single site while the RBCs and WBCs continue to flow.

Typically, the force of a single protein binding event to its receptor is in the order of ~10-11 nano-Newton (nN). Therefore, the attachment force between a CTC and functionalized nanoneedles (where more than $10^3$ protein binding events occur) is more than a few tens of nano-Newton (nN). Now, considering a nanoneedle (50 μm long and 300 nm diameter) with a spring constant of ~$3 \times 10^{-3}$ N/m, the force required to bend a nanoneedle by a distance of 5 μm is ~15 nN. Therefore in this example the specific binding force is enough to bend the needles a few micrometer and complete the circuit between the two opposite electrode which can be readout electrically (FIG. 1c).

In one embodiment, the distance between the nanoneedles in the array is in the rage of 20 μm or more, that is at least 5 μm larger than WBCs, the nanoneedle with an attached cell must bend at least a few micrometers to complete the circuit (FIG. 1c). The force for non-specific binding events is significantly lower. Therefore, in case of attaching WBCs, or RBCs to the nanoneedles, in one embodiment after flushing the device with e.g. Phosphate buffered saline, PBS, the nonspecific binding force is not sufficient to bend the nanoneedles and the electrical circuit remains open. Furthermore, the specific binding may have unique electrical signatures that one can recognize apart from nonspecific binding (e.g. from IV curve or using 1/f measurements).

FIG. 1a shows a schematic of an embodiment of the micro fluidic device (100) as blood is pumped into a dense array of freestanding nanoneedles (101, FIG. 1b) positioned both on the top and the bottom of the channel in this embodiment of the invention. In this example, nanoneedles are conductive and functionalized with antibody (to provide specific binding only for CTCs (103)) and are connected to an electronic readout set up. The remaining interdigitated microelectrodes (areas without the nanoneedles) are coated with an insulating layer.

Figure 2:
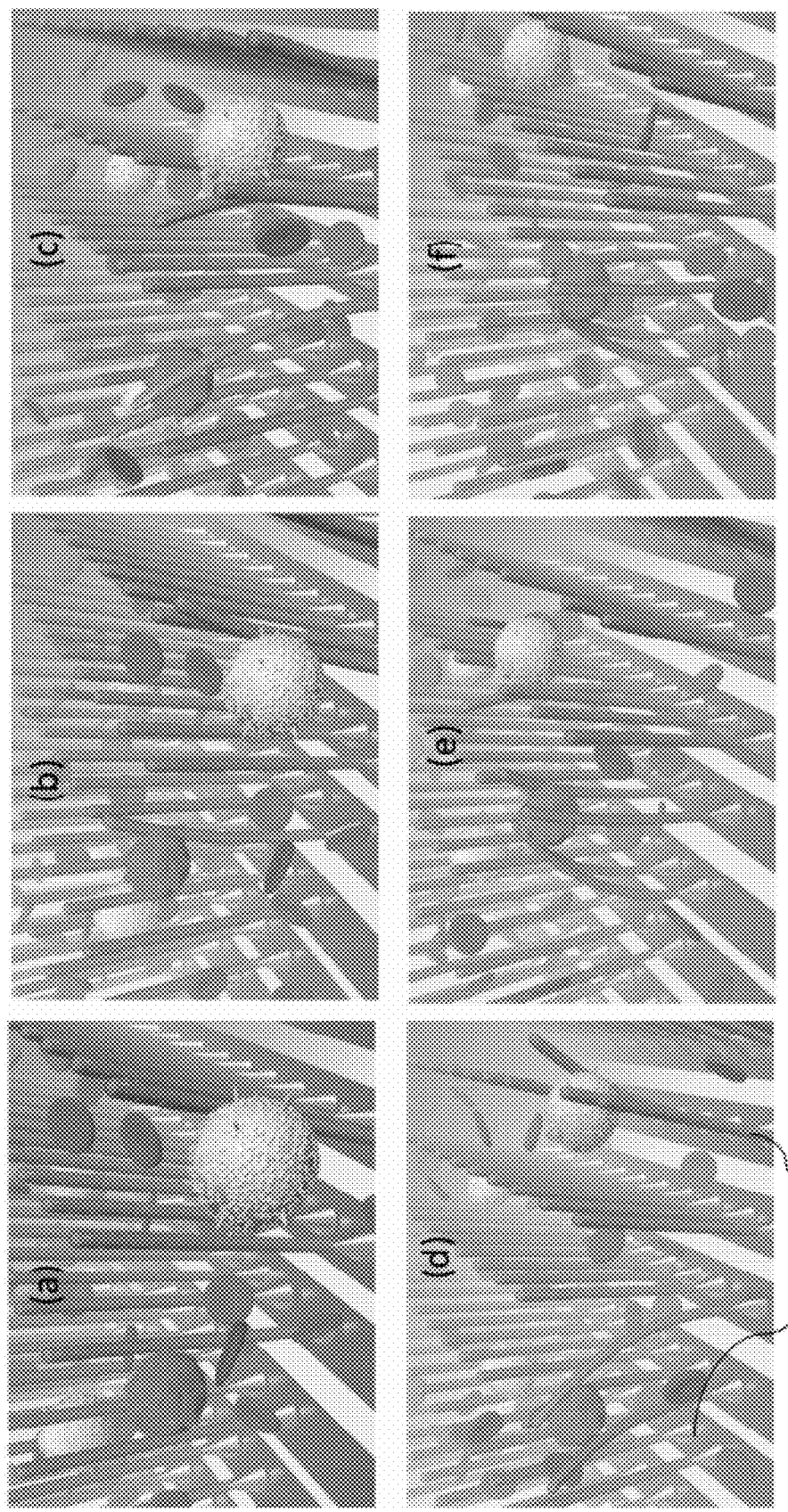
FIG. 2: shows the selective CTC capturing mechanism
Figure 12A:
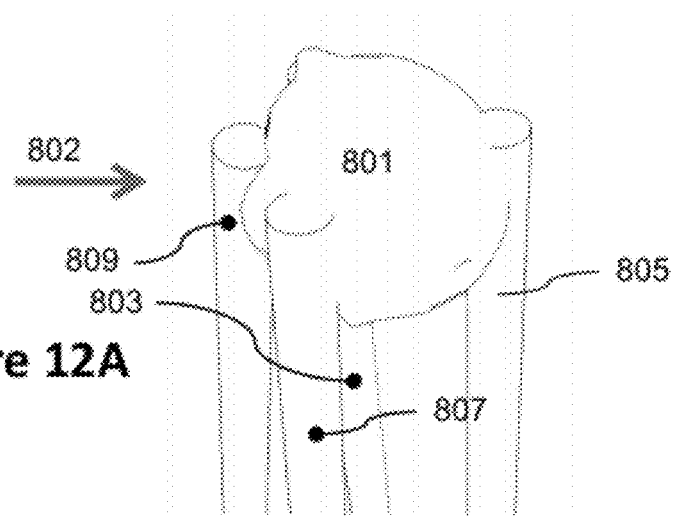
FIGS. 12A and 12B illustrates the contact of the CTC with four nanoneedles as viewed from top and side, respectively.
Figure 12B:
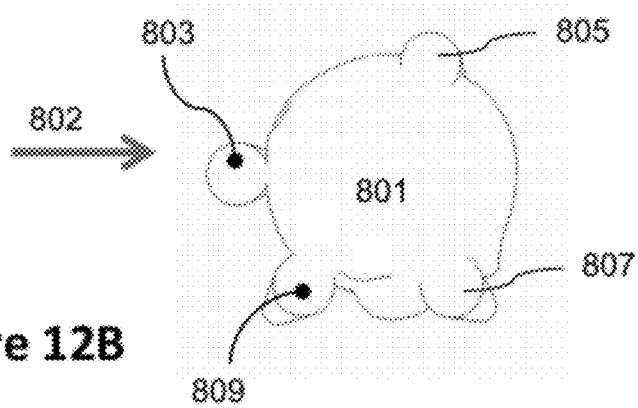

FIG. 2 demonstrate how the example HCTCD (100) selectively capture the CTCs (103) while WBCs and RBCs can pass through the nanoneedles array (101) in this embodiment of the present invention. FIGS. 8 through 12 illustrate the process of capture in more detail. The distance between the nanoneedles are slightly larger than the all the CTCs (801), RBCs and WBCs, therefore as the blood cells flow through the channel (FIGS. 8A and 8B) in the direction 802 and pass between nanoneedles arrays (803, 805, 807, and 809 are four of the nanoneedles which play the main role in capturing/trapping the CTCs (801)) both WBCs and RBCs can pass. Since the nanoneedles are functionalized with antibody (e.g. anti-EpCAM), when a CTC (e.g. MCF7) pass between the nanoneedles array and hit a single nanoneedle (803 of FIG. 8, also FIG. 2a), it is attached to the nanoneedle (803 of FIG. 9, also FIG. 2b). In one embodiment, due to the CTC momentum, the nanoneedle flexes and vibrates back and forth toward the neighboring nanoneedles (805 of FIG. 10, also FIGS. 2c-e). At some point the CTC (801) is in contact with two (as in FIG. 10) then three (as in FIG. 11) nanoneedles and eventually captured by four (FIG. 12) nanoneedles (FIG. 2f), completing the capture process. FIG. 12B shows the nanoneedles are all bent toward each other and captured a single CTC. The nanoneedles are connected to interdigitated electrode (not shown in the FIGS. 8 to 12, but shown in FIGS. 1 and 2). The captured CTC cause the circuit to short and an electrical current is read by a current detector (not shown in the figure).

In one embodiment, since each CTC is captured by two or four nanoneedles in opposite electrodes, it completes the circuit between the two nanoneedles that are connected to an electrical readout that monitors the current. There is at least 800,000 capturing sites available in the device that dramatically increase the chance to capture CTCs with high efficiency and count them via the electrical readout.

NaugaNeedles has developed a set of novel nanofabrication technology platforms. Embodiments of this invention exploits a batch fabrication method to selectively grow ultra high aspect ratio and conductive silver-gallium (Ag2Ga) nanoneedles at any desired locations and orientation on planar or complex three-dimensional substrates. Metallic Ag2Ga nanoneedles have very unique properties including the following. Their electrical resistivity is as low as platinum (105 nΩm). A current density as high as 1.6 A/m2 can be passed through the nanoneedles before melting. The needles are single crystalline with excellent mechanical properties (e.g. can recover their original shape even after being bent up to 50% of the original length). Nanoneedles array can be inexpensively mass produced in ambient condition with control pitch size using very simple optical and micromanipulation setup. Although the nanoneedles are forming at room temperature but remain stable up to 950° C. Also the nanoneedles are highly resistive in corrosive environments (e.g., they can sustain RF plasma etching environments without any measureable change in their morphology).

Fabrication Steps of the HCTCD

Figure 3:
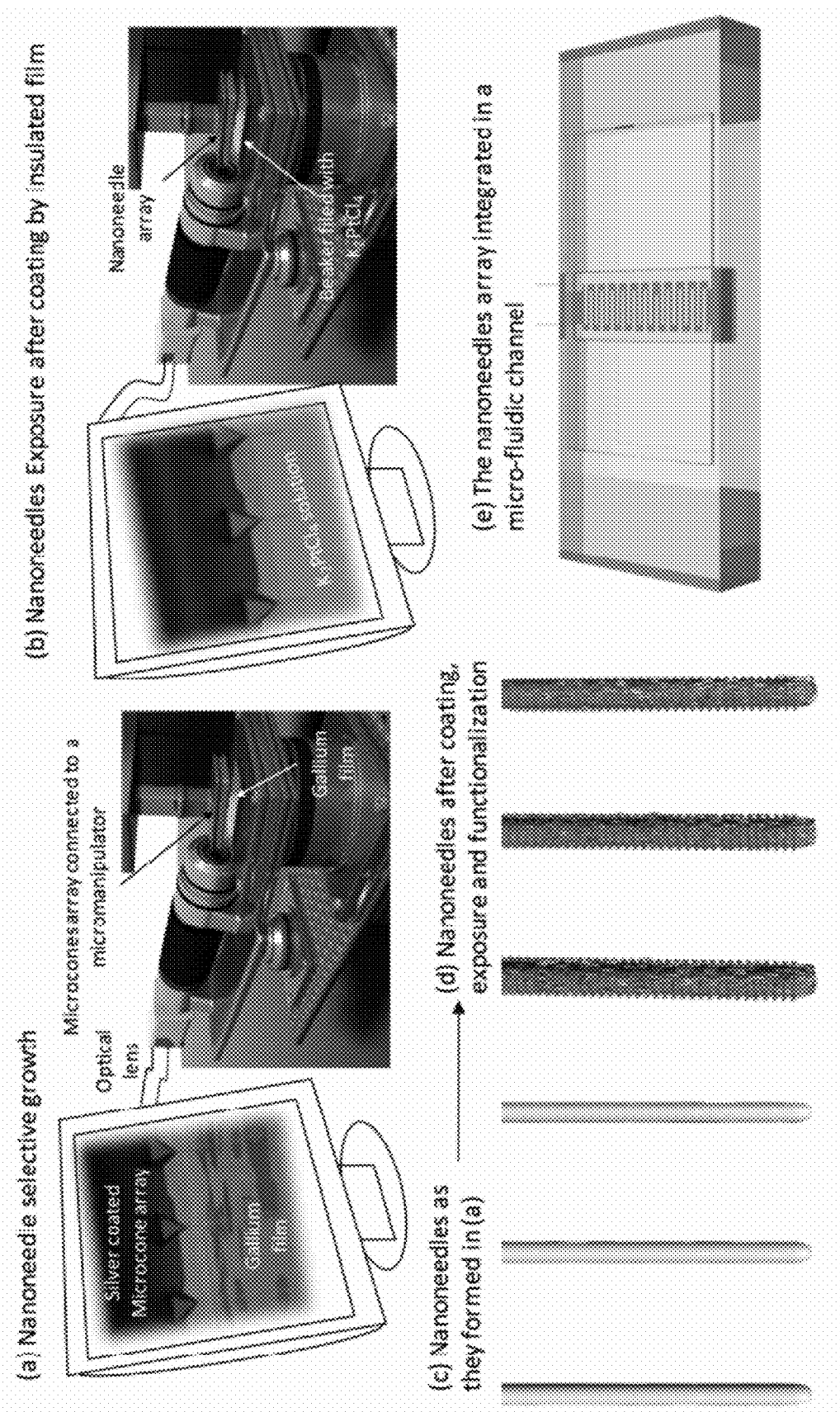
FIG. 3 is a schematic for the fabrication steps of HCTCD.

FIG. 3 shows step by step fabrication of the proposed HCTCD in one embodiment of the present invention:

1. Fabrication of arrays of high aspect ratio metallic nanoneedle on micro electrodes array, using standard micro-fabrication techniques, arrays of silicon microcones that are coated by a thin film of silver pattern is fabricated. The silver pattern is designed in a way to provide an interdigitated array of electrodes that connects every other row of the microcones. The microcones array is brought in contact with a thin gallium film while the approach process is watched by a high resolution camera (FIG. 3a). Gallium interacts with silver film on the cones and dissolves the silver film. By pulling the microcones away from the gallium film, individual freestanding nanoneedles are self-assembled at the end of each microcone to make arrays of very high aspect ratio nanoneedles.

Figure 4:
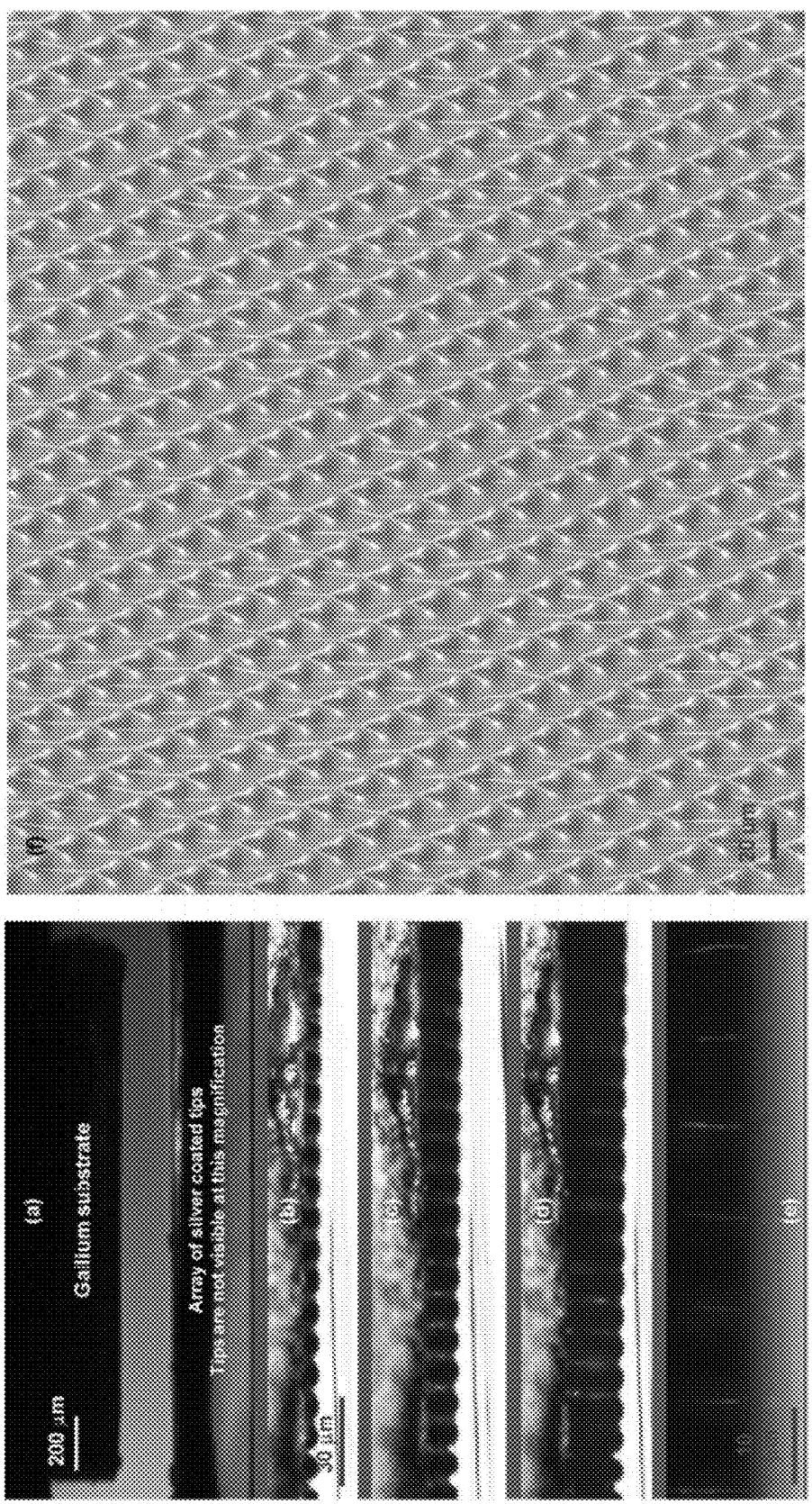
FIG. 4a shows a schematic of Ag2Ga nanoneedles array formation process by dipping silver coated pillar array into a gallium film.
FIGS. 4b-4e show time laps optical images of nanoneedles formation on an array of AFM tip shaped microstructures.
FIG. 4f show SEM image of a high yield nanoneedle growth on microcones array. The process is done using a XYZ micromanipulator under a simple optical setup.

NaugaNeedles has developed a patented batch nanofabrication process and capability to fabricate ultra high aspect ratio freestanding $Ag_2Ga$ nanoneedles at selected location and orientations. FIGS. 4a-e shows an example step by step fabrication of these unique nanoneedles as observed by high resolution optical lenses. A smooth layer of gallium film (FIG. 4a) is approached and aligned with a silver coated array of microcones. The gallium film is then brought in contact with the microcones array (FIG. 4b) and after a few second retracted from the silver array to form array of individual nanoneedles at the tip of each microcones (FIG. 4c-e). FIG. 3e shows a small section of the array as viewed by the operator under a high magnification optical lens. FIG. 4f shows an SEM image of a nanoneedles array form on a 10 μm tall microcones. The distance between the microcones is 20 μm. The growth yield on this particular sample is 97% (489 nanoneedles are formed on 504 microcones). The current average growth rate is 75% that expect to be raised to 90% or more as we practice the fabrication process.

2. Insulated Coating

In one embodiment, the device is then uniformly coated with an insulator layer (e.g. 200 to 300 nm Parylene) through physical vapor deposition. In addition to insulating the microelectrodes, the parylene coating increases the structural integrity, and guaranty the biocompatibility of the device.

3. Nanoneedles Exposure and Functionalization

In one embodiment, the nanoneedles array is dipped into an ionic solution (e.g. 0.05 Molar K2PtCl4 solution, FIG. 2b) in a way that only the needles are submerged. The ionic solution diffuses into the parylene coating, interacts with Ag2Ga nanoneedles, resulting electrically exposing the needles tips and shafts but not the microelectrodes (Also see details in Section 4.1.2). Besides exposing the needle, the parylene films on the nanoneedles swell and become roughen that facilitates the functionalization of nanoneedles by antibody leading to more efficient CTC capturing. In one embodiment of the present invention, the nanoneedles are then functionalized with an antibody (e.g. anti-EpCAM or other antibodies that are specific for CTC cells) to be specific for the CTC (FIG. 3d).

Figure 5:
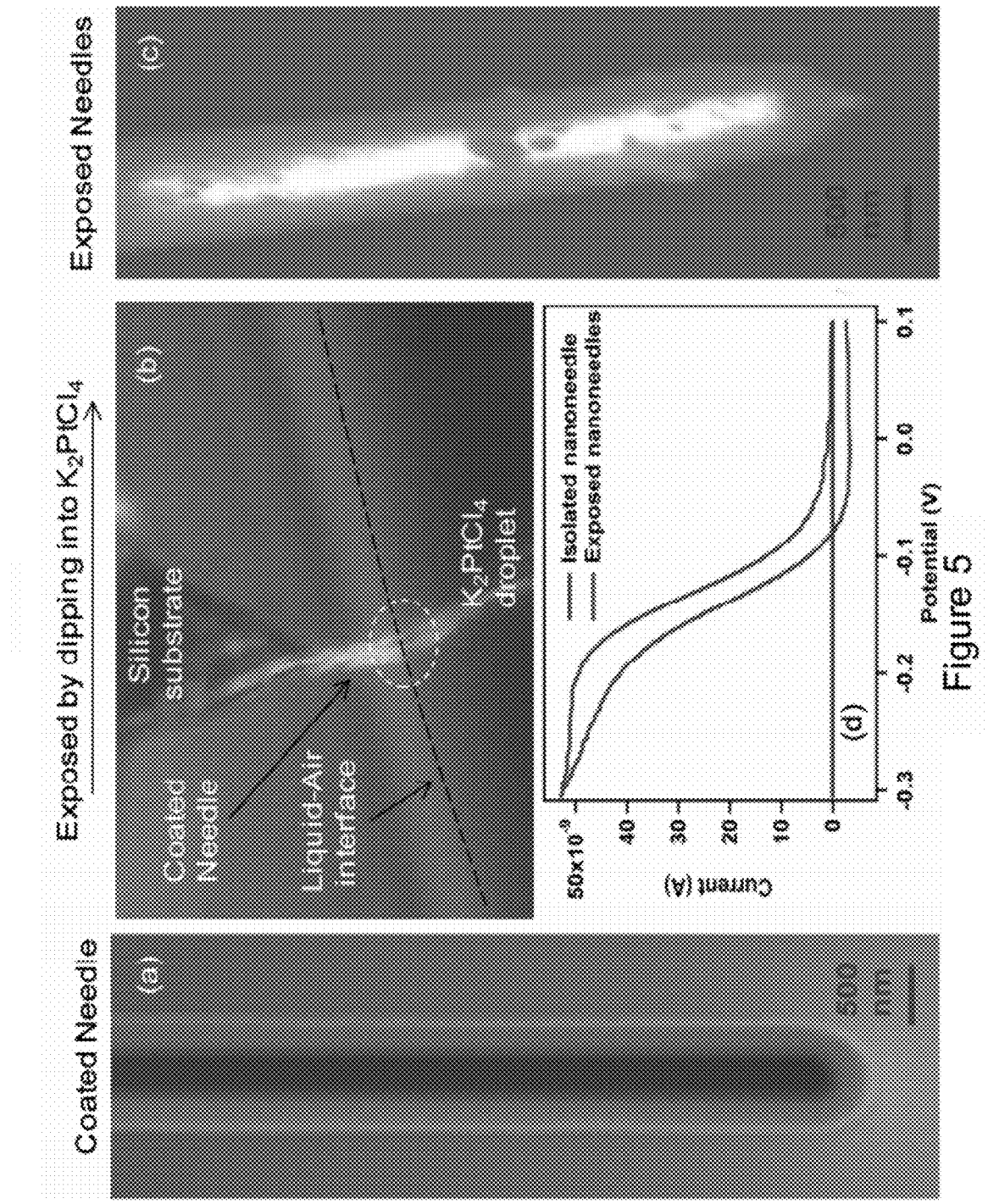
FIG. 5a shows a SEM image of a nanoneedle that is conformally coated with a 200 nm Parylene C.
FIG. 5b shows a coated nanoneedle selectively dipped into a $K_2PtCl_4$ solution.
FIG. 5c shows a SEM image of parylene coated nanoneedles after dipping into $K_2PtCl_4$ for 5 minutes.
FIG. 5d shows CV test before and after dipping a 20 μm long nanoneedle into the $K_2PtCl_4$ solution for 5 minutes.

FIG. 5 illustrates an example method for selectively exposing parylene coated nanoneedles. In this example, a nanoneedle is uniformly coated with a vapor-deposited parylene (poly-xylylene) (FIG. 5a). Then the parylene coated nanoneedles is dipped into a 0.05 Mole of $K_2PtCl_4$ solution (FIG. 5b). Due to the cylindrical geometry of nanoneedles, a stable meniscus is formed between the nanoneedle and the liquid surface. $K_2PtCl_4$ solution diffuses through the pinholes in the parylene film and interacts with the $Ag_2Ga$ nanoneedle. Silver and gallium atoms are exchanged with Pt atoms. In addition, the exchange process results in formation of a coating at the tip of the needle that provides electrical contact to the nanoneedle (FIG. 5c). The process also helps to roughen the nanoneedles tip and shaft that enhances the functionalization process on the nanoneedles.

In one embodiment, to ensure that the exposure process results in formation of an electrode with good conductivity, we have performed cyclic voltametry (CV) on the coated nanoneedles before and after they have been exposed by $K_2PtCl_4$ solution. FIG. 4d shows that after coating a nanoneedle (200 nm original diameter with a 250 nm thick layer of parylene C) the current leakage is on the order of only a few pico-amperes when the entire device is immersed in a 5 mMol of $[Ru(NH_3)_6Cl_3]$ dissolved in 0.1 Mol of $KClO_4$ (FIG. 5d, Blue curve). Repeating the CV curve after dipping the needle (20 μm long) into the solution for 5 minutes, the current increase to 9 nA at −0.2 Volts (FIG. 5d, Red curve). The S shape of the CV curve proof that electrode is fully conductive and has electrochemical properties similar to Platinum. Also, having 50 nA current reveals that the electrode surface area is 78.5 μm2. This surface area is equal to the surface area of a 17.8 μm long nanoneedles with the diameter of 700 nm (200 nm is the original thickness of the nanoneedle plus 250 nm conformal coating). This proofs that the $K_2PtCl_4$ solution has exposed up to 89% (17.8/20) of the parylene coating.

In one embodiment, to chemically modify the nanoneedles arrays, we treat the surface of parylene coated nanoneedles made in Task 1 with 4% volume/volume (v/v) solution of 3-mercaptopropyl trimethoxysilane (Gelest, Morrisville, Pa.) in ethanol for 1 h at room temperature, followed by incubation in 0.01 μmolmL-1 N-y-maleimidobutyryloxy succinimide ester (GMBS) (Pierce Biotechnology, Rockford, Ill.) in ethanol for 30 min at room temperature. This is followed by filling the channels with 10 μgmL-1 NeutrAvidin (Pierce Biotechnology, Rockford, Ill.) solution in PBS for 1 h to attach NeutrAvidin to the GMBS and stored with the avidin at 4° C. until use. 24 h prior to the experiment, 20 μg/mL of any biotinylated antibodysolution in PBS containing 1% weight/volume (w/v) bovine serum albumin (BSA) (Sigma Aldrich, St. Louis, Mo.) and 0.09% (w/v) sodium azide is added to the devices. Ethanol or PBS is used to rinse unbound molecules after each reaction, depending on the solvent used in the previous step. In this embodiment, one hour prior to running the experiment, the devices is purged with 3% BSA with 0.05% Tween 20 (Fisher Scientific, Pittsburgh, Pa.) to block non-specific binding.

4. Micro-Fluidic Packaging for the CTC Detector

In one embodiment, the nanoneedle array (made in steps 1 to 3) is packaged in a micro fluidic channel. To fabricate this channel, standard soft-lithography approaches is utilized to mold the channel structure out of (poly) dimethyl siloxane (PDMS).

5. Electronic Readout

In one embodiment, the electrical monitoring involves measuring the I-V characteristics of the device. A second measurement of using current versus time during blood flow with and without CTC and during and after the PBS flushing is also used for monitoring the time scales involved in the detection. Also, the specific binding events are monitored using 1/f measurements. By using voltage at different frequencies (kHz), the difference between blood cells sitting on a device or cancer cells binding to their receptors in blood due to their characteristic natural frequencies.

The key Advantages of this Embodiment (1) The nanostructured electrodes increase the chance of capturing the cells significantly. The device has over 800,000 capturing sites which increase the device efficiency to almost 100%.

(2) Due to their size, functionality and mechanical flexibility, these capturing sites are specific to only capture CTCs, while RBCs and WBCs pass through the device without being captured.

(3) Due to the large channel cross-section (150 μm height and 20 mm wide) of the HCTCD, the blood flow rate through the channel are very high without losing the efficiency.

(4) The device has an automated readout and no need to be operated by a highly trained professional.

(5) This device is not only applicable in the clinical setting but is also suitable for use in resource limited settings without the need for trained personnel.

Further Activities Supporting the Feasibility of the Example Application

Electrical Properties of Nanoneedles

In a voltage vs. current measurement, we were able to drive a steady state current of up to 5 mA ($1.6 \times 10^{11}$ A/m2) through a nanoneedle with 30 µm length and 100 nm radius. In the same setup, the resistivity of the $Ag_2Ga$ material was measured to be $105 \times 10^{-9}$ ohm-meters (similar to Platinum resistivity). Such low electrical conductivity for the nanoneedle makes them perfect candidates to be used as nanoelectrodes for the capturing sites of the HCTCD.

Figure 6:
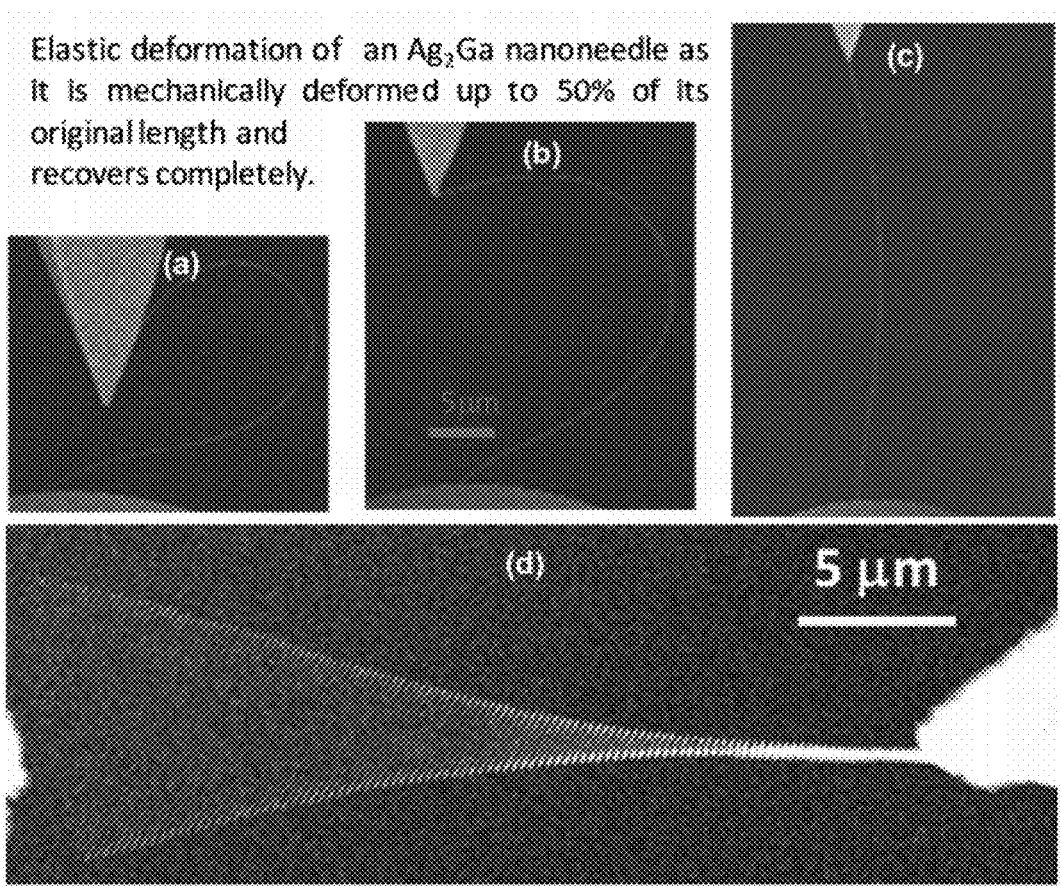
FIG. 6 shows mechanical evaluation of $Ag_2Ga$ nanoneedles including elastic deformation, and electrostatic deflection of the nanoneedles. The vibration frequency is 76.6 KHz and the vibration amplitude of ~9 μm. Therefore the average displacement velocity of the nanoneedles is ~0.69 m/s.
Figures 7A, 7B:
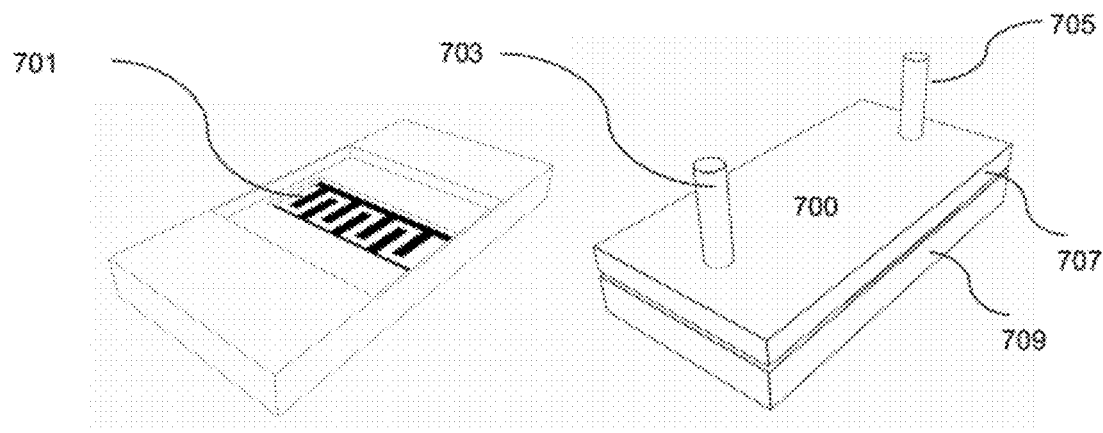
FIGS. 7A and 7B illustrate the CTC detector device as packaged in PDMS moldings.
Figure 9A:
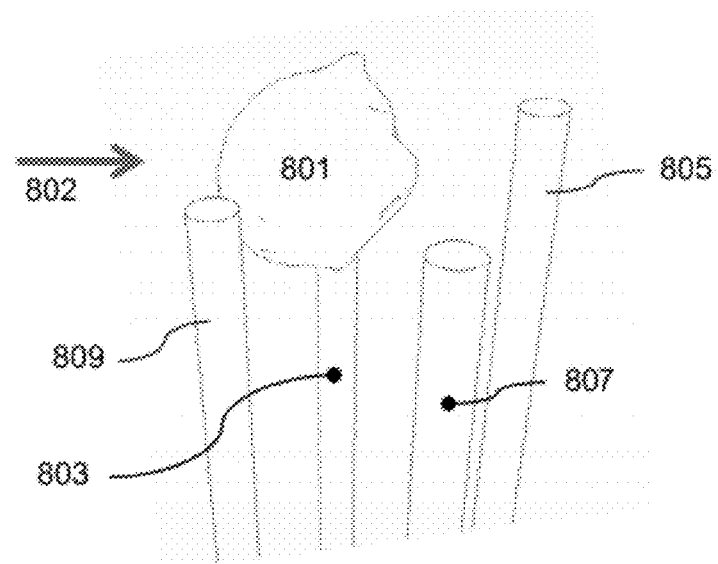
FIGS. 9A and 9B illustrates the contact of the CTC with the first nanoneedle as viewed from top and side, respectively.
Figure 9B:
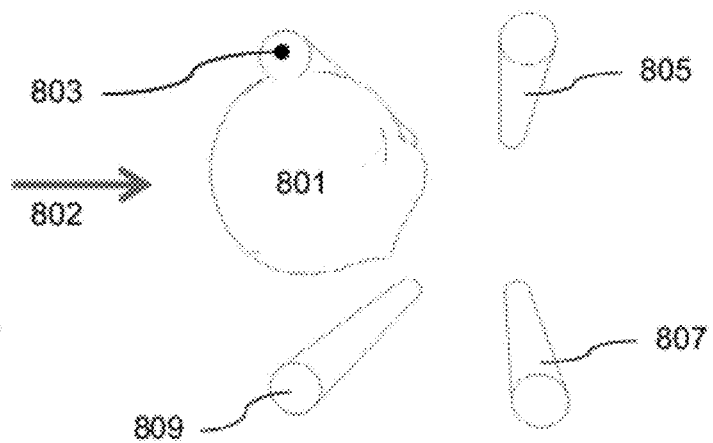
Figure 11A:
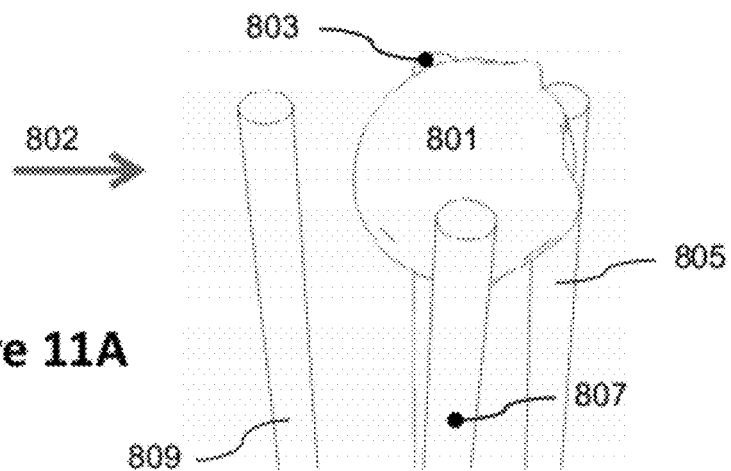
FIGS. 11A and 11B illustrates the contact of the CTC with three nanoneedles as viewed from top and side, respectively.
Figure 11B:
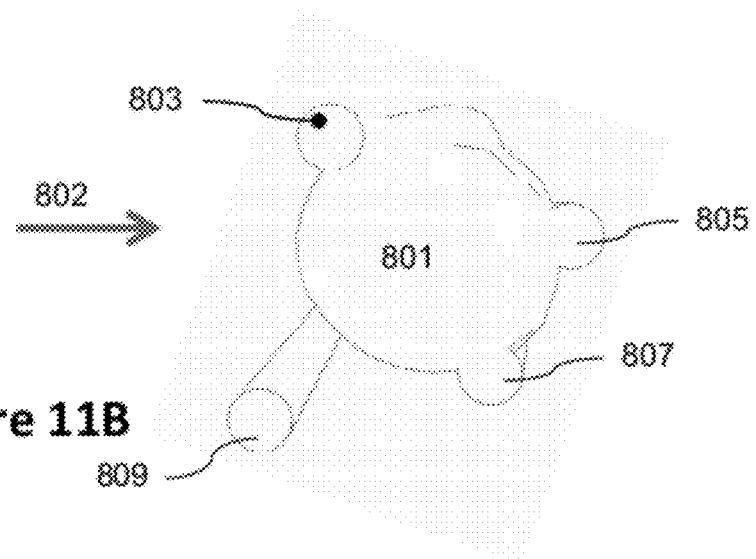

Mechanical Evaluation of Nanoneedles; Perfect Candidates for the Example Device of the Present Invention Due to crystalline structure of nanoneedles, they have excellent mechanical stabilities. FIG. 5 highlights several studies on mechanical properties of $Ag_2Ga$ nanoneedles. In FIGS. 6*a-c*, a nanoneedle, which is clamped from one end, is manipulated by an AFM tip inside an SEM using a nanomanipulator. Even after deforming the nanoneedle up to 50% of its original length the nanoneedles recovers without any plastic deformation.

Nanoneedles also were evaluated via electro-static vibrations over a range of frequencies (FIG. 6*d*). The vibration frequency of this particular nanoneedle shown in FIG. 6*d* is 76.6 KHz, and the amplitude of vibration is 9 µm. Therefore the displacement velocity of the tip of the needles is approximately about 0.69 m/s. The vibration of the nanoneedle was continued for more than 5 minutes without any significance change in shape or properties of the nanoneedle. This observation suggests that the nanoneedles survive during the collusion with the cells as they flow inside the micro channel and collide with the nanoneedles arrays.

In a separate experiment, the Young's modulus of the Ag2Ga nanoneedles is measured to be 84±1 GPa.

Figure 13:
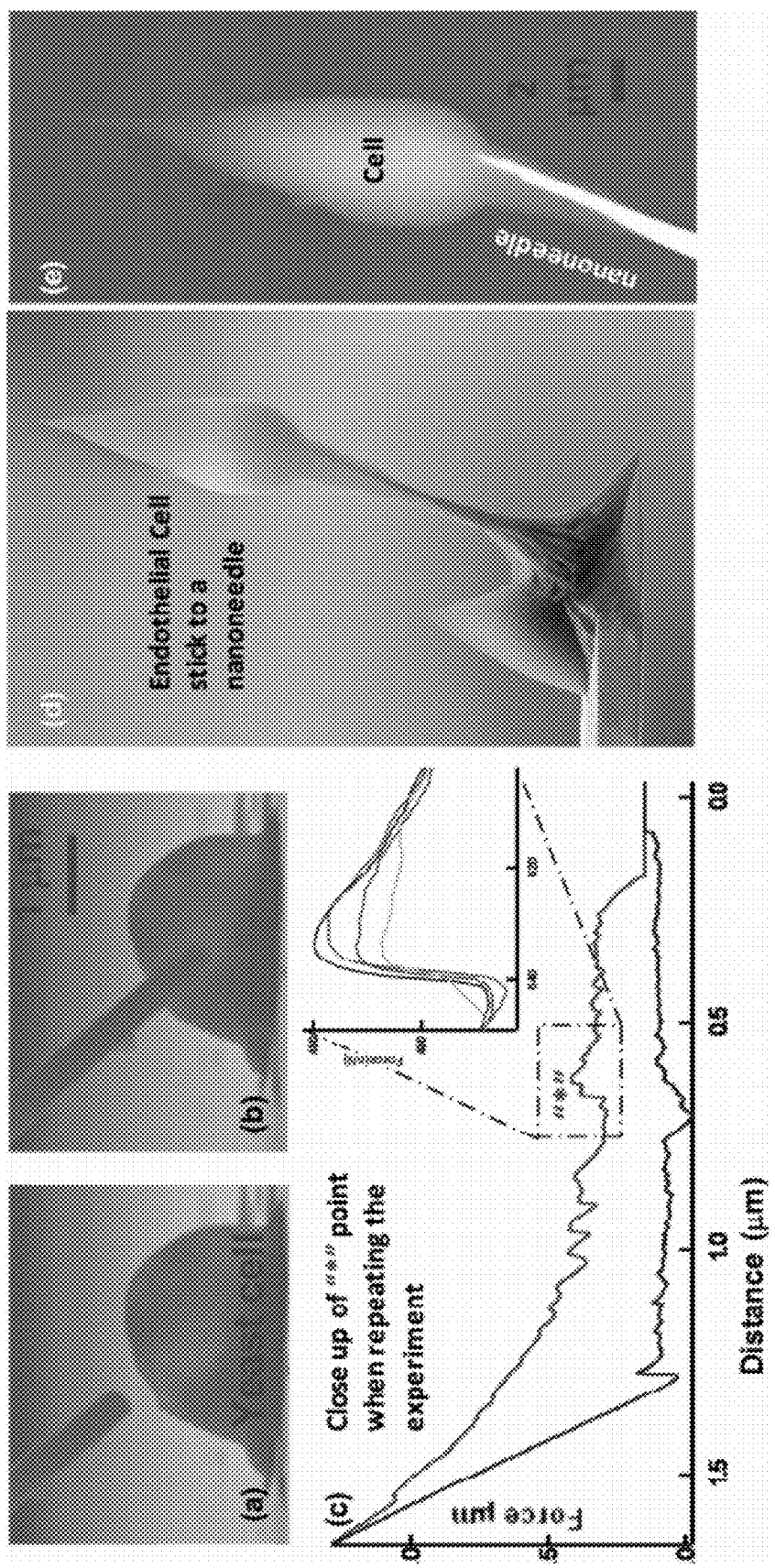
FIGS. 13a and 13b shows Ag2Ga nanoneedle being used to poke into a fixed Yeast cell inside SEM vacuum.
FIG. 13c shows force microscopy in red blood cells in buffered solution.
FIGS. 13d and 13e show an endothelial cell as it has been captured by the needle during AFM force microscopy. The SEM image with the back scatter detector (FIG. 13e) shows the needle inside the cell that reveals the mechanical strength of the nanoneedles.

Nanoneedles Mechanical Stability for Probing and Manipulation of Live and Fixed Cells in One Example Application The mechanical properties $Ag_2Ga$ nanoneedles have been demonstrated to be suitable for probing soft materials, (e.g. cells and liquids). FIGS. 13*a* and *b* show a nanoneedle being inserted inside a fixed yeast cell under SEM vacuum. The high vacuum condition ($10^{-5}$ torr) caused the cell membrane to dry, which increased the difficulty of inserting the nanoneedle into the membrane, but insertion still was achieved. In a similar setup using AFM in buffer solution, force-distance experiments were done on live red blood cells. FIG. 13*c* is a force distance (F-D) curve that shows the extension of the needle into the red blood cell (red curve) and the retraction of the needle from the cell (blue curve). The force curve did not show a significance change, even after repeating the experiment more than 50 times. The inset shows a close-up view of the repetitions of the force experiment at a particular point, "*". Minimal changes occur after each needle penetration, indicating that the cell repairs its membrane after each insertion. The data clearly shows that the RBC does not have any tendency to be attached to the nanoneedle even if we manually push the needle into the cell.

In one embodiment, in a separate experiment, a nanoneedle at the tip of an AFM probe was used to poke into an endothelial cell. Surprisingly the cell immediately wrapped itself aground the needle as it is seen in SEM image in FIG. 13*d*. The closed up view taken by the back-scatter detector in FIG. 13*e* clearly shows that the needle has been buried inside the cell. The SEM images are taken a few hours after the poking experiment that shows the needle can sustain the electrochemical activities of the inside the cell without being decomposed.

In one embodiment of the present invention, a microfluidic device (700) for capturing, and counting the number of, one specific type of cell (e.g. CTC (801)) in a mixture of cells (e.g. white and red blood cells) submerged in a liquid medium (e.g. blood plasma), comprises an array of interdigitated electrodes (701) located on ceiling (707) of the microfluidic device (700), an array of interdigitated electrodes located on floor (709) of the microfluidic device (700), and; a plurality of freestanding conductive nanoneedles (101, FIG. 1) grown on equal intervals on micromachined surfaces of each of the arrays of interdigitated electrodes such that the micromachined surfaces of the interdigitated electrodes on ceiling and floor of the microfluidic device face toward each other. In this embodiment, the freestanding conductive nanoneedles are treated so that the surface of the nanoneedles demonstrate selective adhesion towards the specific type of cell in the mixture of cells (e.g. the CTC), and the area on the interdigiteted electrodes which is not covered by the nanoneedles is electrically insulated, and the distance between the nanoneedles is slightly greater than the largest diameter of any cells within the mixture of cells.

In a further example of the present invention, the nanoneedle arrays are flexible and can bend for several micrometer from their original location without breaking. The nanoneedles of one embodiment of this invention perform actions comprising capturing the specific type of cells by four of the nanoneedles (FIG. 12), where each pair (e.g. one pair can be 803 and 805) of the four nanoneedles (803, 805, 807, and 809) are located on opposing poles of the interdigitated electrodes; and electrically connecting the interdigitated electrodes at the capture site while using the specific type of cell (801) as a medium.

In another embodiment of the present invention, the nanoneedles arrays are metallic and allow for measurement of the resistance of the cells that are captured between two pairs of nanoneedles on opposite electrodes.

Another embodiment of this invention is a method for counting the number of one specific type of cell (801) in a mixture of cells by passing a flow of the mixture of cells in the direction of 802 submerged in a liquid medium through the above mentioned microfluidic device (100, 700). This method comprises: introducing the flow of mixture of cells (802) inside the microfluidic device (700), applying a releasing solution to the nanostructures of the microfluidic device, determining a resistivity value by measuring an electrical resistance between the interdigitated electrodes. In this example, the resistivity value is used to estimate the number of the specific type of cell in the mixture of cells. In one embodiment, the releasing solution is a phosphate buffered saline (PBS) solution.

In a further embodiment of this invention, after applying the releasing solution, the specific type of cell remains strongly adhered to two or more of the nanoneedles and all other types of cells are weakly adhered to any of the nanoneedles.

In yet another embodiment, two or more of the nanoneedles which are strongly adhered to the specific types of cells have different electrical polarities.

In one embodiment, a method of making the microfluidic device, comprises fabricating arrays of high aspect ratio metallic nanoneedle on micro interdigitated electrodes, coating the interdigitated electrodes and the metallic nanoneedles with an insulator layer, submerging only the metallic nanoneedles into an ionic solution to remove the insulating layer from the nanoneedles and not from the interdigitated electrodes, functionalizing the nanoneedles with an appropriate antibody for the specific type of cell, and packaging the nanoneedle arrays and the interdigitated electrodes into the microfluidic device by soft lithography methods.

Any variations of the above teachings are also intended to be covered by this patent application.

The invention claimed is:

1. A microfluidic device for capturing, and counting the number of, one specific type of cell in a mixture of cells submerged in a liquid medium, said device comprising:
    an array of interdigitated electrodes located on ceiling of said microfluidic device, an array of interdigitated electrodes located on floor of said microfluidic device, and;
    a plurality of freestanding conductive nanoneedles grown on equal intervals on micromachined surfaces of each of said arrays of interdigitated electrodes such that said micromachined surfaces of said interdigitated electrodes on ceiling and floor of said microfluidic device face toward each other, wherein said freestanding conductive nanoneedles are treated so that the surface of said nanoneedles demonstrate selective adhesion towards said specific type of cell in said mixture of cells,
wherein, the area on said interdigiteted electrodes not covered by said nanoneedles is electrically insulated, and the distance between said nanoneedles is slightly greater than the largest diameter of any cells within said mixture of cells.

2. The device of claim 1, wherein said nanoneedles arrays are flexible and can bend for several micrometer from their original location without breaking.

3. The device of claim 1, wherein said nanoneedles perform actions comprising:
    capturing said specific type of cells by four of said nanoneedles, where pairs of said nanoneedles are located on opposing poles of said interdigitated electrodes; and
    electrically connecting the interdigitated electrodes at the capture site while using said specific type of cell as a medium.

4. The device of claim 1, wherein said nanoneedles arrays are metallic and allow for measurement of the resistance of the cells that are captured between two pairs of nanoneedles on opposite electrodes.

5. The device of claim 1 for counting the number of one specific type of cell in a mixture of cells by passing a flow of said mixture of cells submerged in a liquid medium through the microfluidic device of claim 1, said method comprising:
    introducing said flow of mixture of cells inside said microfluidic device,
    applying a releasing solution to said nanostructures of said microfluidic device,
    determining a resistivity value by measuring an electrical resistance between said interdigitated electrodes
wherein, said resistivity value is used to estimate the number of said specific type of cell in said mixture of cells.

6. The device in claim 5, wherein said releasing solution is a phosphate buffered saline (PBS) solution.

7. The device in claim 5, wherein after applying said releasing solution, said specific type of cell remains strongly adhered to two or more of said plurality of nanoneedles and all other types of cells are weakly adhered to any of said plurality of nanoneedles.

8. The device in claim 5, wherein two pairs of nanoneedles capture said specific type of cell and said two pairs of nanoneedles which are strongly adhered to said specific types of cells are electrically connected to different electrodes in said interdigitated electrodes and have opposing electrical polarities and wherein said interdigitated electrodes show electrical conductivity between said two nanoneedle pairs.

9. The device in claim 8, wherein the number of specific cells that are adhered to the nanoneedles arrays is proportional to a monitored electrical conductivity between said interdigitated electrodes.

10. The device in claim 8, wherein said mixture of cells in said liquid medium is blood and said specific type of cell in said mixture of cells is of Circulating Tumor Cell (CTC) type.

11. A method of making the device of claim 1, comprising:
    fabricating arrays of high aspect ratio metallic nanoneedle on micro interdigitated electrodes,
    coating said interdigitated electrodes and said metallic nanoneedles with an insulator layer,
    submerging only said metallic nanoneedles into an ionic solution to remove said insulating layer from said nanoneedles and not from said interdigitated electrodes,
    functionalizing said nanoneedles with an appropriate antibody for said specific type of cell, and;
    packaging said nanoneedle arrays and said interdigitated electrodes into said microfluidic device by soft lithography methods.

* * * * *